United States Patent
Bergersen

(10) Patent No.: US 12,424,325 B2
(45) Date of Patent: Sep. 23, 2025

(54) SYSTEMS AND METHODS FOR REMOTE CONTROLLED ORTHODONTIC TREATMENT

(71) Applicant: ORTHO-TAIN, INC., Toa Alta, PR (US)

(72) Inventor: Earl O. Bergersen, Glenview, IL (US)

(73) Assignee: ORTHO-TAIN, INC., Toa Alta, PR (US)

( * ) Notice: Subject to any disclaimer, the term of this patent is extended or adjusted under 35 U.S.C. 154(b) by 0 days.

(21) Appl. No.: 18/460,079

(22) Filed: Sep. 1, 2023

(65) Prior Publication Data

US 2025/0079001 A1    Mar. 6, 2025

(51) Int. Cl.
G16H 50/20    (2018.01)
A61C 7/00    (2006.01)
G16H 10/60    (2018.01)

(52) U.S. Cl.
CPC ............. G16H 50/20 (2018.01); A61C 7/002 (2013.01); G16H 10/60 (2018.01)

(58) Field of Classification Search
CPC ............................... G16H 50/20; G16H 10/60
See application file for complete search history.

(56) References Cited

U.S. PATENT DOCUMENTS

| | | | | |
|---|---|---|---|---|
| 2012/0166213 A1* | 6/2012 | Arnone | ................. | G16H 10/60 705/2 |
| 2020/0312446 A1* | 10/2020 | Katzman | ................ | A61C 7/002 |
| 2021/0077233 A1* | 3/2021 | Yancey | ................ | A61B 5/4547 |
| 2021/0196428 A1* | 7/2021 | Upadhyay | .............. | G16H 50/20 |
| 2021/0361226 A1* | 11/2021 | Yancey | .................... | A61C 7/08 |
| 2022/0313402 A1* | 10/2022 | Katzman | ................ | A61C 7/002 |
| 2023/0386045 A1* | 11/2023 | Amelon | ............... | A61B 5/4547 |

OTHER PUBLICATIONS

"International Search Report and Written Opinion for International patent application No. PCTU24044802, filed Aug. 30, 2024, mailed Sep. 17, 2024, 10 pgs."

* cited by examiner

*Primary Examiner* — Jay M. Patel
(74) *Attorney, Agent, or Firm* — Taft Stettinius & Hollister LLP

(57) ABSTRACT

A system and method for patient diagnosis and implementation of orthodontic apparatuses and treatments. The patient can be located remotely from a remote treatment system, thereby allowing for automatic diagnosis and treatment of the patient without interaction with a medical professional or associated staff. A neural network of an artificial intelligence engine (AI engine) of the remote treatment system can utilize images and other data captured by a patient, as well as patient responses to questionnaires, to derive information regarding the patient's symptoms, and the severity of those symptoms. The AI engine can further be adapted, including via use of historical information regarding a plurality of patients and information from the patient, to obtain a diagnosis and treatment recommendation. The AI engine can further be configured to determine, based on analysis of patient provided images, an appropriately sized orthopedic apparatus, which can be sent to the patient for implementation.

20 Claims, 3 Drawing Sheets

SYSTEMS AND METHODS FOR REMOTE CONTROLLED ORTHODONTIC TREATMENT

FIELD OF THE DISCLOSURE

The present disclosure generally relates to systems and methods for remotely controlled orthodontic treatment, and, more specifically, a remote system that utilizes an artificial intelligence engine in diagnosing and treating patients, including with regards to implementations of orthodontic apparatuses.

BACKGROUND

Patients seeking orthodontic treatment typically physically go to the office or facility of a dental professional, including a sleep clinic, at which the dental professional can obtain and collected certain patient information. Such patient information, or records, can include information obtained via an oral examination of the patient, including, for example, photos/images, measurements, and professional observations, as well as information provided by the patient, including in response to questionnaires, among other forms. At times, such an oral examination can assist the dental professional in assessment various symptom severities, such as, for example, crowding, spacing, overbite, open bite, overjet, presence of a Class III jaw relation, various habits, cross bites, narrow or extra wide arches, temporomandibular joint problems (TMJ), facial appearance, molar relation, and the like. A panoramic x-ray film of the mouth can be taken to determine the presence of several issues such as missing teeth, additional teeth, cysts, and abscesses, among other dental issues. A cephalometric x-ray film may also be taken to determine jaw relations, profile characteristics and tooth inclinations and their positions within the jaw.

The orthodontic treatment process typically involves a patient making numerous in-office visits. For example, the initial examination process can involve one or more visits to one or more offices or facilities, after which a diagnosis is made and treatment options are prepared. Further, in the case of orthodontia, orthodontic devices are affixed to the patient's teeth, and over time the progress of the treatment is periodically monitored in follow up in-office visits, and adjustments are made at in-office visits as needed. These activities are typically carried out in the physical confines of the dental professional's office, requiring the patient to make multiple trips to such location, and require the office to prepare the premises and the various tools used for repeated use. Thus, a substantial amount of time, cost, and operational overhead can be associated with the in-person care, diagnosis, preparation, treatment of patients, and post-visit clean up.

The forgoing difficulties with the nature and logistics of in-patient treatment are exacerbated by the risk physical in-person treatment creates, including with respect to the spread of infectious diseases, such as, for example, SAR Covid 19, among other contagions. This is a risk to both the patient, and the dental professionals administering treatment. Further, substantial additional effort is required to clean and disinfect the premises, equipment, as well as ensuring adequate airflow and purification, in addition to other precautions that must be taken.

Another problem with prior art diagnosis and treatment methods and protocols is that they are subject to the biases and limitations of the treatment professionals. As dental professionals typically rely on their own personal experience, which can be limited or outdated, that experience can introduce biases that can effect diagnosis and treatment decisions. While professional development programs can help, they generally cannot eliminate such problems, particularly in view of the all of the available professional information that one may need to process, retain, and be capable of implementing with skill and expertise. Further, personal predispositions and inclinations also can introduce biases, as the biases can be subconscious and not apparent to the professional, which may make detection and elimination of such biases difficult. Similarly, negative diagnosis and treatments can result from the inevitable lack of the knowledge and experience of the professionals performing treatment, especially those in the early part of their careers.

Additionally, the detection and prevention of fraud in the dental field can be difficult, including, for example, with respect to over-charging and excessive treatment for purpose of generating fees. As a consequence, patients can be subjected to unnecessary treatments and the associated risks, as well as the patients and their insurance providers incurring unnecessary expenses.

Accordingly, there remains a need for further contributions in the field of orthodontia.

SUMMARY

The present disclosure may comprise one or more of the following features and combinations thereof.

An aspect of an embodiment of the present disclosure is a system for remotely diagnosing and treating a patient by a neural network of an artificial intelligence engine. The system can include one or more databases that retain historical patient data corresponding to a plurality of historical patient symptoms, a plurality of historical treatment options, and a historical treatment efficiency for each of the plurality of historical treatment options, each of the plurality of historical treatment options corresponding to at least a combination of a number of historical symptoms of the plurality of historical symptoms and a severity of each of the number of historical symptoms. The system can also include at least one processor and a memory device coupled to the at least one processor. The memory device can include instructions that when executed by the at least one processor cause the at least one processor to receive a patient captured information, the patient captured information being captured by the patient and comprising at least one image, analyze the patient captured information to obtain at least one measurement; receive a patient input response indicating at least a patient condition, compare the at least one measurement and the patient condition to the historical patient data; identify, from the comparison of the at least one measurement and the patient condition to the historical patient data, a recommended treatment option, the recommended treatment option being selected from one of the plurality of historical treatment options; and, communicate the recommended treatment option for retrieval by the patient.

Another aspect of an embodiment of the present disclosure is a method for remotely diagnosing and treating a patient by a neural network of an artificial intelligence engine. The method can include retrieving, by one or more databases, historical patient data corresponding to a plurality of historical patient symptoms, a plurality of historical treatment options, and a historical treatment efficiency for each of the plurality of historical treatment options, each of the plurality of historical treatment options corresponding to at least a combination of a number of historical symptoms of the plurality of historical symptoms and a severity of each of the number of historical symptoms. Further, a patient captured information can be received, the patient captured information comprising at least one image and being obtained by the patient. The method can also include analyzing the patient captured information to obtain at least one measurement and receiving a patient input response indicating at least a patient condition. Additionally, the at least one measurement and the patient condition to historical patient data can be compared, and from the comparison of the at least one measurement and the patient condition to historical patient data, a recommended treatment option can be identified, the recommended treatment option being selected from one of the plurality of historical treatment options. Further, the recommended treatment option can be communicated for retrieval by the patient.

The foregoing outlines rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

These and other features of the present disclosure will become more apparent from the following description of the illustrative embodiments.

BRIEF DESCRIPTION OF THE DRAWINGS

The disclosure described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

Corresponding reference numerals are used to indicate corresponding parts throughout the several views.

DETAILED DESCRIPTION

Figure 1:
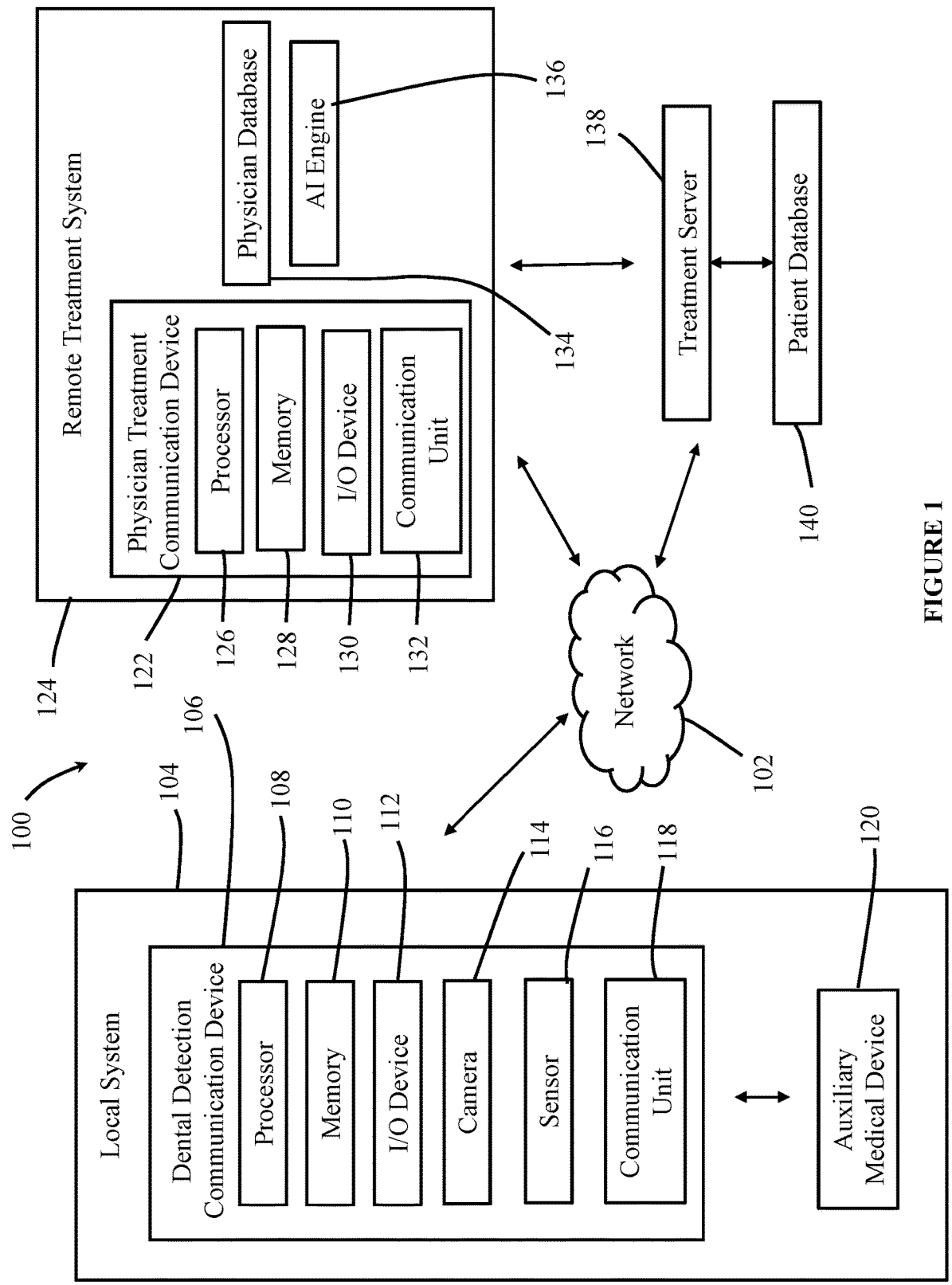
FIG. 1 illustrates a simplified block diagram of an exemplary remotely controlled orthodontic treatment system according to an illustrated embodiment of the subject application.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 4.6, 2, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Additionally, it should be appreciated that items included in a list (whether labeled or numbered or not), in the form of (for purposes of illustration) "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The embodiments of the present disclosure described below are not intended to be exhaustive or to limit the disclosure to the precise forms in the following detailed description. Rather, the embodiments are chosen and described in an exemplary manner so that others skilled in the art may appreciate and understand the principles and practices of the present disclosure.

Embodiments of the present disclosure provide a remote treatment system that can provide medical diagnosis and treatment recommendations to patients without the patient visiting, or directly interacting, with a medical professional. Moreover, embodiments of the present disclosure can utilize a computer implemented method for analysis, diagnosis and treatment of an orthodontic condition. The method can utilize a series of one or more computers under the control of one or more computer programs to provide the analysis, diagnosis, and treatment of the orthodontic condition. Inputs, including those provided by the patient, can be provide information relating to, or used to derive, inputs of initial condition data into the system. Such inputs can include utilizing patient captured information, including images and associated data, to obtain measurements or data on conditions reflective of a state of orthodontic conditions of a patient; diagnoses an orthodontic condition based on the input condition through the use of a computer algorithm;

recommend a treatment to the patient of the orthodontic condition based on the diagnosis; and monitor the treatment by collecting additional data and information from the patient during the course of the treatment.

With the computer programing, such as technological devices and an artificial intelligence engine of the present disclosure, most, if not all, of the above diagnostic procedures and decisions can be made offsite, at least relative to the patient, in an accurate and decisive manner. A computer-generated diagnosis, record taking, and treatment analysis can provide a fast and complete procedure and result for the patient. Further, such an approach can be unbiased and consistent in its conclusions.

The present disclosure therefore provides a benefit of computer based artificial intelligence engine and its ability to diagnose and make treatment recommendations, as well as receive and process observational information about the patient on a routine basis, without the patient making in office visitations and examinations. Further, the present disclosure can provide relatively frequent advice on the progress of treatment of the patient without a patient visit to the office. The present disclosure, therefore, comprises an automatic remote diagnosis and treatment procedure for those cases that are appropriate. Patients that do not fall into the parameters of this treatment procedure are referred to medical professionals or specialists that can more appropriately treat those patients. The system can also be utilized as a diagnostic service by and for the dental professional.

This procedure opens up a new way of treating patients of any age from birth into adulthood with sleep, habit, orthodontic, and speech conditions in a non-biased and cost efficient manner. The orthodontic treatment can also be preventive or interceptive depending on the age of the patient, and moreover whether the patient is 5 to 7 years of age (preventive) or 8 to 12 years of age (interceptive). The disclosure, however, is not limited to treating persons of any particular age, and is adapted to use with patients of any age.

In order to perform the analysis and diagnosis, the system of the present disclosure receives and processes various information from the patient. The information can be collected through a computer interface such as an application operating on a mobile device, or other computer. Information can also be collected through an in-person or remote patient interview process, and/or collected from a questionnaire(s) completed by, or on behalf of, a patient.

The information can then be placed in a database or other suitable electronic storage configuration where the information can be accessed by, and forms the operational basis for, the computer processes, algorithms, and artificial intelligence engine procedures described herein.

FIG. 1 illustrates a simplified block diagram of an exemplary remotely controlled orthodontic treatment system 100 according to an illustrated embodiment of the subject application. The system 100 can be carried out on one or more connected computer systems under the control of computer executed code. The system 100 can comprise a computer/server based analysis system, however, various alternative configurations are also deemed suitable and may employ various computing devices including servers, interfaces, systems, databases, agents, peers, engines, controllers, mobile/handheld devices, or other types of computing devices operating individually or collectively. In some embodiments, various servers, systems, databases, or interfaces exchange data using standardized protocols or algorithms, possibly based on HTTP, HTTPS, AES, public-private key exchanges, web service APIs, known transaction protocols, or other electronic information exchanging methods. Further, such data exchanges can be conducted over a packet-switched network, the Internet, LAN, WAN, VPN, or other type of packet switched network.

Embodiments of the remotely controlled orthodontic treatment system 100 can be carried out under computer control wherein one or more computers carry out the steps of the disclosure via computer programs executing on the processing units thereof. The computers can be linked through various networks such as local area networks, wide area networks, connected networks such as those associated with the Internet, cellular networks, or Wi-Fi networks. The present disclosure can be carried out by a computer program operating on a single computer, such as a desktop, laptop, or mobile device, or on a combination of the foregoing wherein the computer program is distributed between the devices or the program is centrally located on one computer and is able to control the execution of the other devices to carry out the steps of the present disclosure as described herein.

According to certain embodiments, the remotely controlled orthodontic treatment system 100 can connect a variety of different types of located devices that are at different, or remote, locations to each other through any suitable network 102, including, for example, via internet, cellular, and/or WiFi networks. Thus, for example, the network 102 can comprise, for example, personal area networks, local area networks, metropolitan area networks, wireless area networks, wide area networks, virtual private networks, as well as combinations thereof, among other networks.

As shown in FIG. 1, the system 100 can include a local system 104, which can, for example, correspond to a location at which a patient is located. Moreover, according to certain embodiments, the local system 104 may be a location that is different than a location at which an associated medical or treatment professional that is utilizing the system 100 is located. For example, according to certain embodiments, the local system 104 can be the current or temporary residence of the patient, including, but not limited to, the home of the patient.

The local system 104 can also be the location at which a dental detection communication device 106 is at least temporarily located. According to certain embodiments, the dental detection communication device 106 can be a personal computing device of a patient, a patient's guardian, or a personal computing device another resident of, or at, the local system. The illustrated dental detection communication device 106 can take a variety of forms, including, but not limited to, a personal computer, laptop, smart phone, tablet, or mobile computing device, among other computing devices. Further, the dental detection communication device 106 can include one or more processors 108, a memory device 110, and an input/output (I/O) device(s) 112. The processor 108 can be configured to execute software instructions stored on the memory device 110 or other a tangible, non-transitory computer readable storage medium (e.g., hard drive, solid state drive, RAM, flash, ROM, etc.). The software instructions can configure the dental detection communication device 106 to provide the roles, responsibilities, or other functionality as discussed herein.

The I/O device 112 can comprise various types of input devices and output devices, such as, for example, a screen, display, touch screen, keyboard, and/or mouse, as well as combinations thereof, among others. The dental detection communication device 106 can also include at least a camera 114 and, optionally, one or more sensors 116, including, but not limited to, one or more photosensitive sensors, that can be utilized in using the remotely controlled orthodontic treatment system 100 to obtain or capture patient dental related information, including, but not limited to, orthodontic related information and data. Information obtained via operation of the camera 114 and/or the sensor 116 can be compressed via an encoder/decoder of the dental detection communication device 106, among other manners of formatting, for at least transmission, via use of a communication unit 118 of the dental detection communication device 106, to the network 102. Additionally, to assist with the quality of information captured via the camera 114 the dental detection communication device 106 and/or an auxiliary medical device 120 can include a light that is positioned to assist in illuminating the area being captured by the camera 114.

According to certain embodiments, the auxiliary medical device 120 can be a medical device. Moreover, the auxiliary medical device 120 can be a medical device used in the detection and/or treatment of a medical condition. Further, the auxiliary medical device 120 can include one or more of at least one processor, memory unit, I/O device, camera, sensor, and/or communication unit that is/are similar to those discussed herein with respect to the dental detection communication device 106. For example, according to certain embodiments, the auxiliary medical device 120 can be an intraoral wand, photosensitive sensor, sonar sensor, digital scanning device, among other devices. Further, the auxiliary medical device 120 can be configured to transmit information obtained by the auxiliary medical device 120 to the network 102, such as, for example, via a local network. Alternatively, the auxiliary medical device 120 can communicate such information to the dental detection communication device 106, which can directly or indirectly communicate the information to the network 102.

The remotely controlled orthodontic treatment system 100 is adapted to accommodate communications between the dental detection communication device 106, or an auxiliary medical device 120 of the local system 104, with a physician treatment communication device 122 at, or associated with, a remote treatment system 124. The remote treatment system 124 may be remote from the local system 104, and thus from the dental detection communication device 106 and/or the auxiliary medical device 120. For example, according to certain embodiments, while the local system 104 may correspond to a residence of the patient or the patient's guardian (collectively referred to herein a "patient"), the remote treatment system 124 can correspond to an office, hospital, clinic, or other facility of a medical professional that is providing medical assistance to the patient, including, for example, dental or orthodontic related assistance. Additionally, or alternatively, the remote treatment system 124 can correspond to a residence of the medical professional. Thus, the remote treatment system 124 can be at a location that is different than the location of the local system 104.

As seen in FIG. 1, the remote treatment system 124 can include the physician treatment communication device 122. The physician treatment communication device 122 can be generally similar to the dental detection communication device 106. Accordingly, similar to the dental detection communication device 106, the physician treatment communication device 122 can include, as well as be a combination of, personal computers, laptops, smart phones, tablets, or mobile computing devices, among other computing devices. Thus, similar to the dental detection communication device 106, the physician treatment communication device 122 can include one or more, if not each, of a processor 126, memory device 128, I/O device 130, and communication unit 132 that can be similar to the processor 108, memory device 110, I/O device 112, and communication unit 118 that were discussed above with respect to the dental detection communication device 106.

The remote treatment system 124 can also include a physician database 134 and an artificial intelligence (AI) engine 136. The physician database 134 can include a variety of records and patient forms, as well as the corresponding form templates. The records in the physician database 134 can thus, for example, include information, including, but not limited to, images, videos, measurement and other data that may have been obtained via use of the dental detection communication device 106 and/or the auxiliary medical device 120, including but not limited to, via use of the camera 114 and/or the sensor(s) 116. Additionally, the physician database 134 can also include other information provided by the patient from at least the dental detection communication device 106, including information inputted by the patient into forms provided by, or accessible from, the remote treatment system 124. As discussed below, such information maintained by the physician database 134 can be used to train, including continue to train, a neural network of the AI engine 136 (generally collectively referred to herein as the AI engine 136). According to certain embodiments, in addition to, or in lieu of, the physician database 134, the system 100 can include a patient database 140, which may be at a remote location relative to at least the remote treatment system 124. The patient database 140 can record at least some of the same information as that discussed above with respect to the physician database 134. Thus, information from the patient database 140 can also be utilized in the training of the neural network of the AI engine 136. According to certain embodiments, the patient database 140 is a cloud based database, or may be part of a datacenter that maintains records for a variety of other affiliated or unaffiliated, medical professionals, including, but not limited to, dentists, orthodontists, and oral surgeons, among other medical professionals.

According to certain embodiments, the system 100 can also include a treatment server 138, which may, or may not, be part of the remote treatment system 124. The network 106 can provide a pathway for the dental detection communication device 106 and the physician treatment communication device 122 to have access to a treatment server 138. The treatment server 138 can include a processor, a memory, and a network interface. For example, the treatment server 138 can include a data information system, data management system, web server, and/or file transfer server. The treatment server 138 can also be a workstation, mobile device, computer, cluster of computers, set-top box, a cloud server or other computing device. In an embodiment, multiple modules may be implemented on the same treatment server 138. The treatment server 138 can also, for example, be part of a data center or be a cloud based server. The treatment server 138 can also include software, firmware, hardware, or a combination thereof. Software may include one or more applications on an operating system. Hardware can include, but is not limited to, a processor, memory, and/or graphical I/O device display. According to certain embodiments, the server 138 can be used in connection with website that can provide an interface between the patient and a medical professional. For example, according to certain embodiments, such a website can be utilized in connection with providing an interface that the patient can use to upload information that was attained via use of the dental detection communication device 106 and/or auxiliary medical device 120. Further, the system 100 can be configured such that information uploaded from at least the dental detection communication device 106 and/or auxiliary medical device 120 can be stored at either, or both, the physician database 134 and the patient database 140.

The AI engine 136 can be an AI based decision engine that can utilize various parameters and factors to generate a diagnosis and treatment protocol, including determining the apparatuses appliances that a patient is to utilize in at least an attempt to achieve a desired outcome. The AI engine 136 can be based on a neural network that comprises a series of nodes that behave similar to neurons, in accord with system control. The nodes can be in communication with one another. The nodes can take input data to perform small operations on data, the results of such operations being passed to other nodes. In the present disclosure, various measures of the conditions of dentition of patient, as described, for example, below, can each provide input information to one or more of the nodes in the form of a scaler value representing a degree of severity of the patient's condition. These measures can include the diagnostic information gleaned from images, photographs, sonar, video, and the like taken from a patient's dentition, as obtained, for example, via the use of the dental detection communication device 106 and/or auxiliary medical device 120, as wells the information from the forms, questionnaires, points bases scores, and other evaluations described herein. Again, such information can, for example, be accessible to the AI engine 136 from either, or both, the physician database 134 and/or the patient database 140, as discussed above.

The nodes can be highly interconnected elements, sometimes called "neurons" as an analog to the neurons in the human brain. The nodes are organized in layers that process information using dynamic states in response to the external inputs described above. This structure can be very useful in uncovering efficient patterns of conditions that can be correlated to the most effective treatments using the apparatuses or appliances, among other tools, described below. The patterns can be introduced to an AI nodal network by an input layer, which can have a node assigned for each input value. The inputs can then be communicated through the neural network to internal nodes, which are sometimes can be referred to as hidden nodes since they operate "unseen" between the input nodes and nodes that output the end result. The internal nodes can apply weights and biases to the input values to scale the importance of the inputs in absolute terms, and relative to each other. Once the input values are received by a node, a weighted sum of the values can be calculated using the biases and in accord with a pre-determined activation function (such as a sigmoid, σ, or ReLu function). The function can then determine if the cumulative normalized value meets a predetermined threshold that determines if the node should be activated (or fired) thereby sending an output response to the next connected nodes in the network. This process can continue until all of the information from the input nodes and internal nodes has been processed through the neural network, until at the end of this process the last layer of nodes linked to the output layer provides its output, the firing of which can determine an action that can correlate to a specific diagnosis for a patient along with the treatment protocol.

In more particular detail, the internal nodes can accept inputs from one or more nodes in the neural network, apply weights to the inputs that reflect the importance of the input value, then sum the values and typically add or subtract a bias, and compare that to a threshold. If the threshold is exceeded, the node is said to have fired and it passes that information on to the next nodes in the neural network. If the threshold is not exceeded, the node does nothing.

The output of the node can be further refined using a sigmoid of other similar function. However, it may not be advantageous to give a node representing a set of input values an all or nothing response, but instead provide a continuous response between some values (such as 0-1). In this manner, the function moderates the output such that small changes in input values will not result in large changes in output where that can disproportionately affect the end result.

The weights and biases are adjusted or tuned through a process of evaluation/training to determine the appropriate importance to assign to various input parameters. This can be done through a supervised learning or a training process, where the AI engine 136 or neural network can be given a set of initial conditions, initial weights, biases, and functions, and the output treatment decision is reviewed by a professional for correctness. The various weights, biases, and functions are then adjusted until the AI engine 136 arrives at the correct result as based on professional review of the results.

More precisely, a formula can be used to quantify how close the output of the AI engine 136 is to a desired result, as determined by a supervised learning expert(s). This function is sometimes referred to as a cost function, and many versions exist and can be used, including a mean squared error function. Further, linear error functions can be used, but may require refinement as such functions may not differentiate well between large and small errors. An output error can be back propagated through an algorithm that can take into consideration a gradient of the cost function. The backpropagation can adjust the weights and balances of each of the inputs to reduce the error between the actual result and the result achieved by the AI engine 136.

The AI engine 136 can also use other techniques and methods to enhance the predictive efficiency of the AI engine 136. The AI engine 136 can use supervised or unsupervised learning algorithms. Under supervised learning template data models of the various symptoms and conditions can be provided that are subject to treatment in accord with the present disclosure. These models can be used to detect issues based on their classification when compared to actual patient data. This approach can work well with issues that have a relatively well-defined and measurable criteria for detection and correction. Alternatively, or additionally, regression techniques can be utilized that can quantify issues amenable to more probability based outcomes. The AI engine 136 in these cases can use one or more various algorithms to match a patient's information to a model within a predetermined measure of probability or accuracy. Those algorithms can include regression, classification, naive Bayes classifiers, K-NN (nearest neighbors), decision trees, support vectors, and the like.

The AI engine 136 can also use unsupervised learning techniques to work with data that has not been labeled or classified, and where the AI engine 136 or neural network makes its own determinations. Such an approach can utilize algorithms to find patterns through clustering techniques that look for clusters in data that self-segregates. Alternatively, such an approach can use association rules learning, which can look for patterns where one trait is associated with another, which can provide a basis for making predictions based on associations and trait correlations.

The AI engine 136, or neural network, can also us convolutional AI algorithms, which can be particularly useful in processing images, including three-dimensional (3D) images, that may be obtained, for example, the dental detection communication device 106 and/or the auxiliary medical device 120. Such algorithms can use one or more convolutional layers, where a convolving scan of the input image is conducted with one or more filters. The filters can be applied section by section to the input image to detect some shape or feature of, or in, the image, and pass that information on to the next layer in the algorithm. Initial convolution layers can use basic filters to detect edges or curves, which are then passed on to layers that can detect patterns that are more complex. The AI algorithms can also use one or more pooling layers to conduct dimensional reduction, reducing the number of parameters in the input. The pooling layers can use convolving scans and a filter, but can also include simpler reductions like filtering for a max pixel or average pixel intensity value over the scanned section, and can be useful in reducing complexity, noise suppression, and the like. Further, sets of convolutional and pooling layers can be used. Eventually, fully connected layers can be used that can connect the output of the convolution and pooling layers with the input information.

Other AI based algorithms can be used as well, including for processing images that may have been provided by the dental detection communication device 106 and/or the auxiliary medical device 120, such as dense nets, regional convolution neural networks (R-CNN), or single shot multibox detector algorithms (SSD), which can detect images and also regions within images (such as can be used to detect the relationships between teeth).

The AI engine 136 can be configured to utilize various combination of the above-discussed techniques, as some conditions, particularly patient conditions and/or information available to the AI engine 136, may be more amenable to certain techniques than others.

Figure 2:
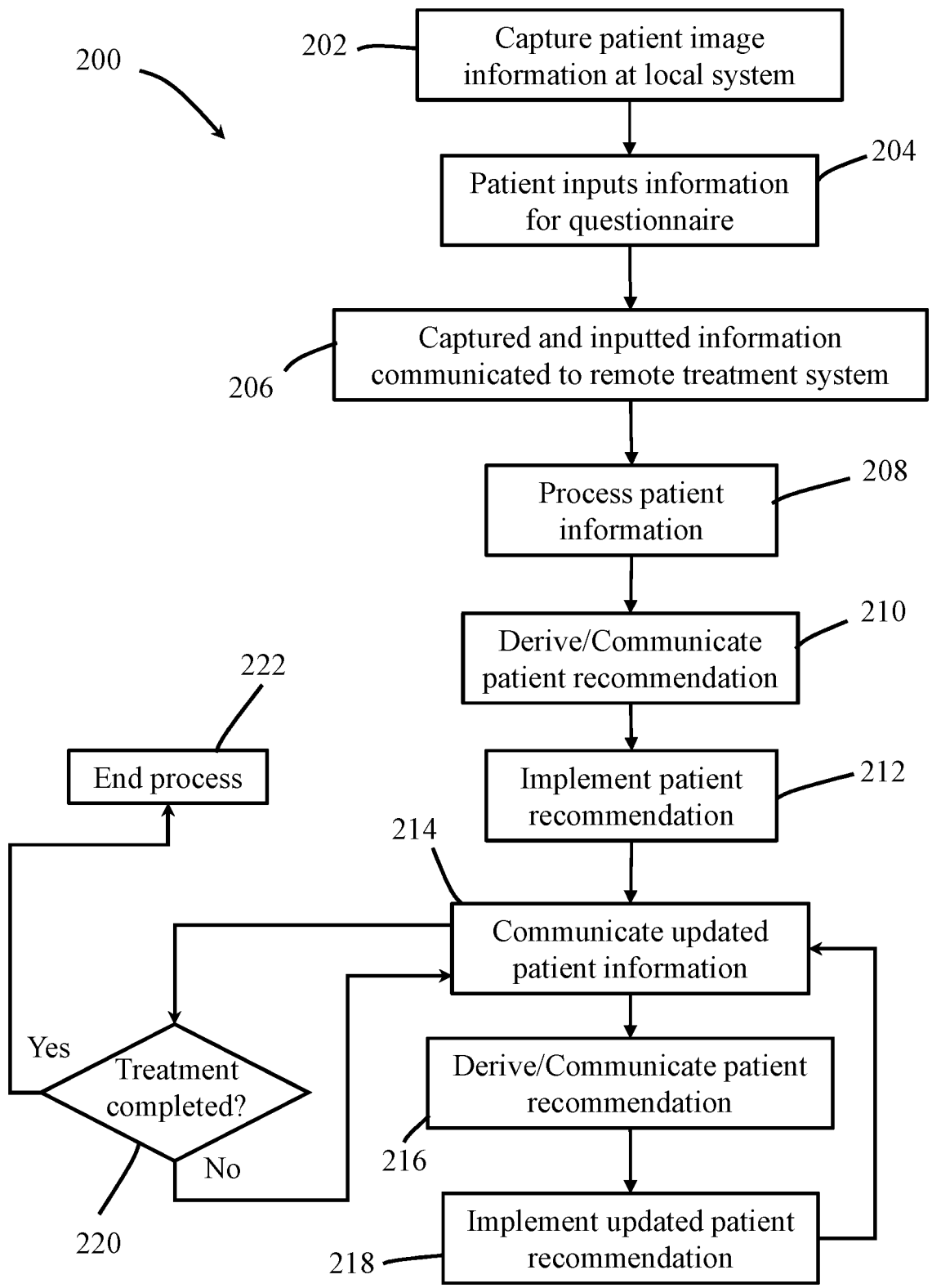
FIG. 2 illustrates a simplified flow diagram of a method for diagnosing and treating a patient that can be performed using at least the exemplary remotely controlled orthodontic treatment system shown in FIG. 1.

FIG. 2 illustrates a simplified flow diagram of a method 200 for diagnosing and treating a patient that can be performed using at least the exemplary remotely controlled orthodontic treatment system shown in FIG. 1. The method 200 corresponds to, or is otherwise associated with, performance of the blocks described below in the illustrative sequence of FIG. 2. It should be appreciated, however, that the method 200 can be performed in one or more sequences different from the illustrative sequence.

At block 202, a patient at the local system 104 can capture patient information via use of the dental detection communication device 106 or the auxiliary medical device 120. The patient information captured at block 202 can correspond to patient image information, including for example, an image(s) captured via use of the camera 114 and/or sensor 116 of the dental detection communication device 106. Such images can be used to derive one-to-one images of the teeth directly from the mouth, as well as other dental and/or orthodontic features related to teeth, the mouth, and/or the jaw. Further, according to certain embodiments, the captured information, such as images, can provide images of the patient's dentition or face, among other information. Additionally, various imaging producing procedures can be used at block 204 to capture the dentition from various views, such as, for example, frontal and lateral images of the dentition, as well as occlusal views of the upper and lower arches. The various images captured at block 202 and provided by the patient can be used by the remote treatment system 124, including the AI engine 136, to determine a variety of information. For example, such image information and the associated data from the patient can be used by the AI engine 136 to determine measurements of the overbite, overjet, severity of crowding, displacement of teeth (crowding), spacing, open bites, molar relations, gummy smiles, broken contacts, and/or cross bites, among other information.

According to certain embodiments, the patient information captured at block 202 can be patient image information, including, for example, one or more images and videos. More specifically, in certain applications, the captured patent image information can include one or more of a series of still digital images, photographs, sonar, or a video of the teeth or dentition of a patient. The patient information provided at block 202 can also include, but is not limited to, x-ray or sonar films such as panoramic films and cephalometric films.

Further, in association with at least attempting to improve the quality of the information provided in the patient captured information, block 202 can include the system 100, such as, for example, the remote treatment system 124 and/or the treatment server 138, providing, or providing access to, a self-instructed digital viewing guide of the dentition.

In at least certain instances, the patient can receive instructions, such as for example, from the remote treatment system 124, of the manner in which the patient is to capture the patient image information. For example, in at least certain instances, capturing the patient image information via video can be advantageous, as such video can provide a plurality of individual views for the remote treatment system 124, including the AI engine 136, to select for analysis. Further, in comparison to video, a series of individual photos may offer a more limited selection of view. However, such photos can be adequate if a reasonable variety of views are provided and the quality of the images in the photos are sufficient for analysis by the remote treatment system 124, including, for example, by the AI engine 136. Thus, according to certain embodiments, block 202 can indicate, for example, the format, type, and number of images that are to be captured by the patient, as well as provide instructions as to the areas and/or manner in which the patient is to capture such information, among other instructions.

While the foregoing is discussed in terms of photographs and video, additionally, or alternatively, patient image information captured at block 202 can include information captured by the sensor(s) 116 or the auxiliary medical device 120. For example, according to certain embodiments, the patient image information captured at block 202 can be obtained from an intraoral wand, photosensitive sensors, or by sonar transmission of the dentition, or similar digital scanning device, which can provide a one-to-one image of the patient's dentition.

At block 204, the dental detection communication device 106 can also be utilized to provide inputted patient information. For example, such information can be obtained from the patient inputting information into the dental detection communication device 106 via use of the I/O device 112. Further, such information can be inputted into the dental detection communication device 106 in response to questions or inquiries in one or more forms provided by the remote treatment system 124 and/or the treatment server 138, as previously discussed. As indicated by the below discussion, the type of information requested at block 204 can include information that may not be derived from captured images or sensed data.

For example, according to certain embodiments, at block 204, the patient can be instructed to perform certain tasks that provide information used in the assessment and determination of relatively reliable conclusions as to patient condition. For example, information provided at block 204, and/or block 202, can be used to connection with an identification of a temporomandibular disorders (TMD/TMJ problems), Class III pseudo or skeletal problems, the severity of the tonsils, habits such as abnormal swallowing, tongue thrusts, improper tongue resting position, thumb sucking, snoring, mouth breathing, and the like. Information provided at block 204 can include information provided by the patient as requested by a multi-symptom questionnaire, which may be a general questionnaire and/or a questionnaire directed to particular conditions, including for example, dental, sleep, speech, and/or breathing issues, as well as any combinations thereof. Such patient inputted information can be utilized by the remote treatment system in connection with diagnosing the patient, and providing associated recommendations, as discussed below. Moreover, such patient inputted information can, for example, be utilized by the remote treatment system 124 in connection with diagnosing and/or providing treatment recommendations with respect to at least sleep, speech, nasal breathing issues, and other needs that can be addressed through orthodontia.

Information provided at 204 can include indicating which teeth the patient has, or does not have. For example, diagram similar to a tooth numbering system diagram can be provided to the patient to use in indicating which teeth are, or are not, present. The diagram can also be provided to the patient as a basis for indicating which tooth/teeth the patient may be experiencing a problem.

Block 204 can also include the patient providing diagnostic information, including, for example, information regarding patent habits (e.g., anterior tongue thrust, thumb/finger sucking, swallowing problems, nail biting). Other information requested regarding the patient can be directed to the presence of a temporomandibular joint (TMJ) disorders (e.g. clicking, pain, opening and/or chewing difficulties), tonsil swelling, pseudo and skeletal Class III jaw relations, breast and bottle feeding, pacifier usages, speech lessons, sleep and speech questionnaires, and the like. The requested information can be accompanied by written instructions and/or visual depictions that can assist in the understanding of the questions being asked and/or evaluating the patient. Additionally, while some answers may elicit binary responses (e.g. yes or no, true or false), other responses can seek an indication of severity. For example, when providing the presence, or absence, of a condition or symptom, the response may be provided in the form of a severity level or scale (e.g. 0=not present or N/A; 1=very mild, 2=mild, 3=moderate, 4=pronounced, and 5=severe). The particular information being requested by the form can also be based on different patient characteristics, including, for example, the age of the patient. Questions may also seek information regarding any neuro-diverse characteristics of, or diagnosis for, the patient.

Information provided at block 204 by the patient can also include information regarding normal or abnormal breathing. For example, at block 204 the patient can be asked to provide information regarding: approximately 63 symptoms that relate to abnormal sleep, approximately 24 symptoms relating to speech, 56 questions regarding various patient habits, TMJ issues, Class III jaw relations and tonsil swelling.

The information obtained at either, or both, of blocks 202 and 204, can occur in connection with onboarding, or initial diagnosis and treatment of the patient, as well as during a course of an observation or treatment. For example, the patient can capture or otherwise provide such information periodically, including, for example, at certain time intervals, which can be predetermined intervals, including, for example, over the course of a predetermined number of days, weeks, and/or months. Additionally, the system 100 can be configured such that the dental detection communication device 106 receives reminders of when the patient is to capture and provide more recent information in connection with blocks 202 and 204. As discussed below, such updated information can be analyzed by the physician treatment communication device 122 and/or the AI engine 136 in assessing patient progress, if any, in response to current or past treatment, and provide recommendations as to whether the current course of treatment should continue, be modified, or changed, including, for example, with respect to pursuing another course of treatment.

At block 206, the information obtained at block 202 and/or block 204 can be communicated to the remote treatment system 124, including the physician database 134, and/or the patient database 140, and, at block 208, the communicated information can be retrieved and processed, including, for example, by the remote treatment system 124. According to certain embodiments, the patient information is provided electronically to a portal, where the information can be retrieved by the remote treatment system 124 for analysis, including, for example, analyzed to quantify all the various measures, dimensions, and occurrences in comparison to reference data to determine the relative severity or deviation from optimum, and make treatment recommendations, determine fees, and other treatment details are calculated.

The analysis at block 208 can include the AI engine 136 and/or the physician treatment communication device 122 quantifying various measures, dimensions, and occurrences, as well as comparison of such details with reference data to determine the relative severity or deviation from optimum. Further, as discussed below, such an analysis can be accompanied by the AI engine 136 and/or the physician treatment communication device 122 making treatment recommendations, determine fees, and calculating other treatment details.

According to certain embodiments, such processing at block 208 can be done using a diagnostic program, which may, for example, be stored on the memory device 128 of the physician treatment communication device 122, and which can be aided by the AI engine 136. Moreover, the diagnostic program can, with the assistance of the AI engine 136, review at least the patient captured information, such as the images and/or video. For example, in at least certain instances, the retrieved patient captured information can be used to analyze the dentition and the malocclusion, if any, of the patient. Such analysis can, for example include, but is not limited to, measurements that can be attained from, for example, the patient captured information. Such a process, including the foregoing mentioned measurements, can include obtaining, via operation of the processor 126 and/or AI engine 136 various dimensions and relations from the actual images provided by the patient captured information, which can include, for example, images of all the teeth in the mouth. Further, such an analysis can detect potential dental related issues, including the extent or degree of such dental issues, that can relate to, for example, overbite, overjet, crowding, rotations, spacing, arch widths, available and required spaces, Class III malocclusions, and open bite, as well as combinations thereof, among others.

The information available to the remote treatment system 124, including the physician treatment communication device 122 and/or the AI engine 136 can be relatively numerous. For example, according to certain embodiments, the remote treatment system 124 can receive via blocks 202 and/or 204, over around 190 variable and inputs that are analyzed by the remote treatment system 124. As discussed below, such variables and inputs can be used by the remote treatment system 124 to obtain an accurate and reliable diagnosis in a relatively short time period (e.g., within seconds), as wells recommendation(s) with respect to treatment appliances. For example, according to certain embodiments, using information provided by, as well as accessible to, the physician treatment communication device 122 and/or the AI engine 136, the physician treatment communication device 122 and/or the AI engine 136 can derive a recommendation of one or more orthopedic apparatuses that are to be used for the patient, including, but not limited to, an orthopedic apparatus(es) that can treat, improve, and/or to correct abnormal sleep and/or orthodontic symptoms that may be harmful to a patient's wellbeing and/or appearance.

According to certain embodiments or circumstances, the communicated information can be used to calculate tooth size. For example, a tooth size of the teeth of the patient, such as mesio-distal widths, among others, can be calculated by the remote treatment system 124, including, for example, via use of the physician treatment communication device 122, and which can be aided by the AI engine 136, from 1:1 dimensional images produced by camera 114, sensors 116, and/or auxiliary medical device 120, including, but not limit to sensor or sonar images. Additionally, or alternatively, such tooth sizes can be obtained by actual dimensional measures taken at the same time as the information is captured by the dental detection communication device 106 and/or the auxiliary medical device 120. Further, the tooth sizes determined by the remote treatment system 124 can correspond to a true size of the tooth, including, but not limited, to a true size of the associated front tooth of the patient.

The remote treatment system 124 can also be configured to utilize information attained from, or via use of, the remote treatment system 124 regarding the size of one or more teeth to determine the size of other teeth, if not all other teeth of the patient. For example, as tooth widths are highly correlated, information stored by the remote treatment system 124, including, for example, charts, can be used to determine of sizes of other teeth accurately from the width of another tooth, such as, for example, a lower incisor. Additionally, with respect to teeth which may typically present more variation in anticipated tooth size, compared to other teeth, including, for example, upper lateral incisor, actual sizes can be compared to charted values to determine any variation.

The remote treatment system 124, including the physician treatment communication device 122 and/or the AI engine 136, can use tooth sizes, including, for example, tooth width, as determined or otherwise obtained via use of the remote treatment system 124, to determine a size of a space in the mouth of the patient that can accommodate the teeth, and/or an available space that can be a size of a space in the patient mouth that may be needed for the teeth to be straightened.

For example, the remote treatment system 124 can utilize at least the widths of the four lower or upper incisors to determine a size of a space in the mouth of the patient that can accommodate the teeth. If a width of one lower adult permanent lower central is determined, or measured, the remote treatment system 124, including, for example, the physician treatment communication device 122 and/or the AI engine 136, can utilize charts, models, or expressions, to determine the widths of the four lower adult incisors. Such a configuration of the remote treatment system 124 can enable the remote treatment system 124 to estimate the required space needed to have a straight incisal dentition at the end of treatment.

The AI engine 136 can also be configured to examine different images, or types of images for different issues or features. For example, the AI engine 136 can be adapted to examine panoramic x-ray images for about nineteen potential items or issues, and examine cephalometric and hand x-ray films for about fifty-four other issues, as well as for around ten other miscellaneous items. Thus, according to certain embodiments, the AI engine 136 can be trained to look for particular issues or features that may appear in certain image types, and/or with respect to images of certain features or views.

In certain instances, the inputted patient information, including information obtained at block 202 and/or block 204, may not be clearly defined, which can complicate the ability of the remote treatment system 124, including, for example, the physician treatment communication device 122 and/or the AI engine 136, to determine corresponding information, including determining sizes and/or shapes, among other information. Moreover, in such cases, the physician treatment communication device 122 and/or the AI engine 136 can be configured to include techniques to assist in arriving at an estimated size, shape, or configuration. For example, in at least certain instances, a space(s) that exists for the teeth to be straightened, or available space, can be difficult to determine if the actual arch circumference from one canine to the other along the incisal edges of the lower incisors along the curvature of the arch is not clearly defined in the images provided via the inputted patient information, and/or cannot be measured by the remote treatment system 124. The physician treatment communication device 122 and/or the AI engine 136 can thus be configured to include techniques to assist in arriving at an estimation for the available space by using a series of straight-line measures or triangles around curved areas. The available space can then be accurately determined by the physician treatment communication device 122 and/or the AI engine 136 from an occlusal view of the arch, which can be used to determine appliance sizes when compared to the required space. While, in such an example, there may be many multiplication factors that can be used, the physician treatment communication device 122 and/or the AI engine 136 can be configured to utilize the factors that may be considered to provide an anticipated higher level or degree of accuracy. Thus, in the discussed example the physician treatment communication device 122 and/or the AI engine 136 can be configured to utilize factors that are based on lower incisor widths, as the widths of the lower incisors are typically very consistent when comparing these widths to each other.

The processing of patient information at block 208 can thus, according to certain embodiments, result in the remote treatment system 124 determining, or estimating, the available space(s) in the patient's mouth needed for straightening a tooth or teeth of the patient, as well as an overall size of a space for the patient's teeth. Further, a comparison of the overall size of a space for the patient's teeth and the available space can provide an indication of whether there is, or is not, an issue with crowding, or overcrowding, of teeth.

At block 210, the physician treatment communication device 122 and/or the AI engine 136 can utilize at least the information analyzed at block 208, as well as other information that may be stored in the physician and/or patient database 140, to arrive or output patient outcome. Such an outcome can include, for example, outputting one or more suggested or recommended corrective actions, including, for example, treatment actions.

For example, such size and/or crowding information, as well as the above-discussed determinations regarding tooth/ teeth size, can be utilized at block 210 by either or both the physician treatment communication device 122 and/or the AI engine 136 in selecting, or providing a recommendation of, an appropriate orthodontic apparatus. Further, system 124 can also accurately measure the dentition for the correct size or type of the treatment appliances. For example, currently there are about fifty different standardized sizes of orthodontic appliances depending on tooth size differences in four various appliance designs. Thus, at block 210, according to certain embodiments, after the physician treatment communication device 122 and/or the AI engine 136 size information regarding the tooth/teeth, available space, and/or crowding is determined at block 208, the physician treatment communication device 122 and/or the AI engine 136 can, at block 210, select an image of a selected orthodontic appliance and digitally place the image of the selected orthodontic appliance over an image, such as, for example, a photograph, that was provided as inputted patient information at block 204. Such placement, or overlaying, of the image of the selected orthodontic appliance on an image of the teeth of the patient can allow the physician treatment communication device 122 and/or the AI engine 136 to verify whether a proper size of orthodontic appliance had been determined. For example, as orthodontic appliances are substantially transparent, the physician treatment communication device 122 and/or the AI engine 136 can, via the digital placement of the orthodontic appliance relative to the image of the teeth of the patient, compare or analyze the size(s) of the orthodontic appliance against an outline(s) and/or perimeter(s) of the tooth images through various image producing procedures.

In addition to determining the size of the orthodontic appliance to be used, the physician treatment communication device 122 and/or the AI engine 136 can, at block 210, also be utilized to determine if additional orthodontic appliances are to be recommended and/or employed with another orthodontic appliance(s), an estimated direction such an orthodontic appliance(s) is to be utilized, including worn, by the patient, an expected likelihood of success if the orthodontic appliance(s) is worn for the recommended duration, and/or a duration that the same orthodontic appliance should be used for retention of alignment of the teeth.

Additionally, or alternatively, the diagnosis and/or recommendations provided at block 210 can also be reviewed by an overseeing medical professional, such as, for example, a dentist. Such oversight can be used to at least confirm to make sure the diagnosis and appliance sizes, as determined by the AI engine 133 and/or the physician treatment communication device 122 at least appear to be correct, or for other reasons. However, the operation of the system of the present disclosure is not necessarily dependent on such oversight or review by a medical professional. Moreover, embodiments of the subject disclosure can accommodate patients receiving recommendations, and/or an associated treatment, without requiring intervention of a treating professional or representative. However, in at least certain embodiments, the opportunity for patients to have access to consultation may be provided to address questions, special conditions, or supervisor concerns dictated by caution or any professional standards.

At block 212, according to at least certain situations, the recommendations provided at block 210 can be implemented. For example, at block 212, the orthodontic appliance(s) recommended at block 210 can be installed in the patient's mouth, or otherwise be used by the patient. Such implementation can also include communication of the recommendation to the patient. For example, the recommendation from block 210 can be communicated via the communication unit 132 of the physician treatment communication device 122, and the network 102, to the communication unit 118 of the dental detection communication device 106. According to certain embodiments, implementation at block 212 can include sending, shipping, and/or delivering the orthodontic appliance(s) to the patient, after which the patient can install the orthodontic appliance(s). Thus implementation can, according to certain embodiments and/or scenarios, occurs remotely from the location of the associated medical professional, such as, for example, dentist or dental technician, among others.

Periodically, including, for example every month or two, a reevaluation can occur. For example, similar to the discussion above with respect to at least block 202, the patient can use the camera 114 or sensor(s) 116 of the dental detection communication device 106 and/or the auxiliary medical device 120, and/or provide other information similar to that discussed above with respect to block 204. The updated information can, similar to the above discussion with respect to at least blocks 206 and 208, further be communicated to, and processed by, the remote treatment system 124, to the remote treatment system 124, including, for example, the physician treatment communication device 122 and/or the AI engine 136. Thus, at block 214, the updated information can, alone or in view of the information provided at block 202 and/or block 204 can be utilized by the physician treatment communication device 122 and/or the AI engine 136 to determine the extent, if any, progress in treatment is, or is not, occurring, and/or whether the progress, or lack thereof, is different that had anticipated, such as, for example, estimated at block 210.

Additionally, or optionally, based on the outcome of the analysis or diagnosis at block 214, at block 216 the physician treatment communication device 122 and/or the AI engine 136 can generate an updated recommendation, such as, for example, with respect to continuing, adjusting, or changing the current course of treatment. For example, at block 216, the physician treatment communication device 122 and/or the AI engine 136 can provide a recommendation for a change in usage of the orthodontic apparatus(s) that has been implemented, and/or provide a recommendation with respect to a change in the orthodontic apparatus(s). Thus, progress is below expectations, the physician treatment communication device 122 and/or the AI engine 136 can recommends changes so as to attain, or maintain, the proper progress that will result in an anticipated orthodontic correction and outcome.

Additionally, at block 216, the updated or revised recommendation, if any, can be communicated to the patient. For example, according to certain embodiments, the information can be communicated, via the network 102, from the remote treatment system 124 and/or via the communication unit 132 of the physician treatment communication device 122 to the dental detection communication device 106, wherein the information can be outputted to the patient via the I/O device 112 of the dental detection communication device 106.

As with block 210, the recommendations provided at block 216 can be, but is not necessarily, reviewed by an overseeing medical professional.

At block 218, similar to block 212, the updated recommendation, if any, can be implemented. Such an implementation can, for example, adjusting an orthopedic appliance(s) that the patient has been using, and/or installing or otherwise using another orthopedic appliance(s). Further, similar to block 212, such implementation can involve shipping or otherwise delivering an orthopedic appliance(s) to the patient at the local system 104 such that the patient can install and/or use the orthopedic appliance(s).

Thus according to certain embodiments, the AI engine 136 can determine when different orthopedic appliances are required, including, for example, as a result of further eruption of permanent molars. Thus, block 218 can include the system 124 automatically sending, or making available, the appropriate updated orthopedic appliance to patient. For example, for at least certain patients, during the course of treatment, there may be as many as four orthopedic appliances that the patient may use. However, additional appliances can be recommended by the system 124, including, for example, in response to the patient developing or having other problems, such as, for example, problems relating to maxillary deficiency, overgrowth of the mandible, rotations of certain teeth, and/or either or both sleep and speech needs. Further, the AI engine 136 can automatically prompt the patient, or the patient may otherwise provide, information to determine patient compliance with wearing the recommended appliances. If compliance is inadequate, the system 124 can inform the patient of the problem, and advise on any corrective action.

In at least certain events, and/or after a certain period of time or treatment, at least the physician treatment communication device 122 and/or the AI engine 136 can determine, at block 220, whether treatment is to be concluded. Such a determination can be based, at least in part, on the progress of the treatment and/or current condition of the patient, as can be reflected in at least the information provided at block 214. Further, a determination of whether treatment is completed can, but is not necessarily, reviewed and/or approved by an overseeing medical professional, If treatment is to continue, then the patient can continue with providing at least periodic updates at block 214. However, if treatment is to be discontinued, the process can end at block 222. Such an ending at block 222 can include communicating to the client that the course of treatment is completed, and, optionally, may include an overall progress report reflecting the accomplishments, if any, of the treatment.

Figure 3:
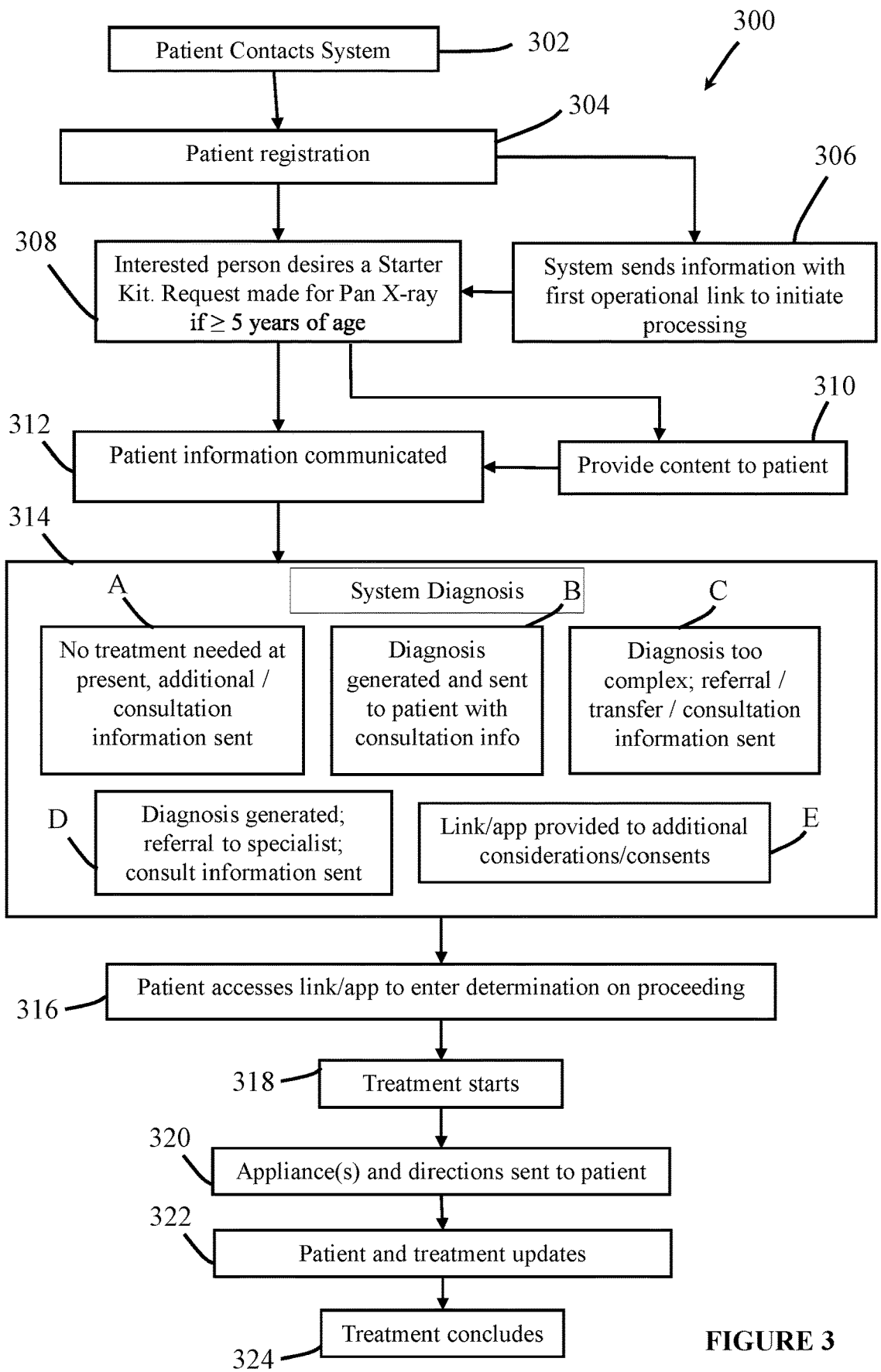
FIG. 3 illustrates a simplified flow diagram of a technical processing system and method of the present disclosure.

FIG. 3 illustrates a simplified flow diagram of a technical processing system and method 300 of the present disclosure. The method 300 corresponds to, or is otherwise associated with, performance of the blocks described below in the illustrative sequence of FIG. 3. It should be appreciated, however, that the method 300 can be performed in one or more sequences different from the illustrative sequence.

At block 302, the patient can connect to the system 100, including, for example, by establishing a connection from the dental detection communication device 106 to the treatment server 138 and/or physician treatment device 122 via the network 102. As previously discussed, the term patient can, for example, refer to the actual patient or a representative of the patient, including, for example a parent, guardian, or care provider, among others, of the patient. Thus, such a connection at block 302 can, for example, involve opening an internet web page and creating an account, responding to requests for information on the web page, or providing the information through a software application ("app.") operating on the dental detection communication device 106.

At block 304, the patient can provide general information, such as, for example, information that can register the patient with the remote treatment system 124. Such information may or may not be related to a particular medical, including, for example, dental condition of the patient. Moreover, the information provided at block 304 can relate to general patient onboarding, such, for example, identification, contact, and/or insurance information, among other information. Additionally, at block 304, the patient can request information, such as, for example, information regarding particular treatments that may be offered by the associated medical provider associated with the remote treatment system 124, and/or regarding pricing, among other information.

The information collected from the patient at least at block 304 can be communicated to the remote treatment system 124, treatment server 138, and/or patient database 140, where the information can be placed in the physician database 134 and/or patient database 140 and indexed to the patient's account, name, or other indicia of identification. At block 306, with at least the information provided at block 304, the remote treatment system 124 can provide the patient with information about how to proceed with processing, treatment options, educational information, and administrative matters. According to certain embodiments, the information provided at block 306 can be accessible via a link or to a web address that is accessible via use of the dental detection communication device 106, or through the application running on the a dental detection communication device 106. Alternatively, the information from block 306 can be sent to the patient through the mail.

At block 308, the patient can respond to the information provided at block 306. For example, the patient can response by requesting a starter kit. Additionally, an indication can also be made as to whether arrangements are to be made to obtain images of the patient that the patient may not themselves be able attain. For example, the patient and/or the remote treatment system 124 may need to arrange an appointment for the patient to obtain an image(s) that may involve certain specialized medical equipment, which can constitute, for example, an the auxiliary medical device 120, as shown in FIG. 1. Thus, such an the auxiliary medical device 120 may include, for example, equipment of a medical professional, clinic, or service that can provide a panoramic radiograph or x-ray of a patient's mouth and/or teeth, among other images. Whether the patient is to obtain such specialized images can depend on a variety of factors, including, for example, the nature of the treatment being sought and/or the age of the patient, including, for example, whether the patient is, is older than, five years of age.

At block 310, in response to the patient request made at block 308, information, instructions, and/or a medical device(s) that may be sent either electronically to the dental detection communication device 106 and/or physically sent to the patient, such as, for example, via mail. For example, at block 310 the patient may receive a starter kit, which can include one or more questionnaires. The questionnaires can relate to a variety of different types of issues, including, for example, sleep, speech, and dental issues, among others. The questionnaires can also be based, at least in part, on an age of the patient. Thus, patients of different ages or age ranges, and/or seeking different types of treatment, may receive different forms or questionnaires. Thus, information provided, for example, at block 304 and/or 308, can provide an indication of which particular form(s) or questionnaires the remote treatment system 122 is provide to the patient at block 310. Additionally, the information being sought from the patient by the forms or questionnaires provided to the patient at block 310 can be generally similar to the information discussed above with respect to block 204 of FIG. 2.

The starter kit, or other content provided at block 310, can also include, or provide instructions for obtaining, a particular medical device that may assist the patient in later obtaining and providing patient specific information, including images, to the remote treatment system 122. For example, according to certain embodiments, at block 310, the patient may receive a check retractor, among other medical devices.

Block 310 can also include information or instructions regarding the type of information that is to be captured by the patient, and/or whether the patient will need to utilize both, or either, of the dental detection communication device 106 and/or the auxiliary medical device 120. For example, block 310 can provide instructions regarding the patient obtaining, or capturing, information such as that discussed above with respect to block 202 of FIG. 2. Block 310 can further include the patient capturing such information, such as, for example, via use of the camera 114 and/or sensor(s) 116 of the dental detection communication device 106 and/or via an auxiliary medical device 120.

At block 312, responses to the information requested at block 310, including responses to the questionnaire(s) or form(s), as well as images captured by or for the patient via the dental detection communication device 106 and/or via an auxiliary medical device 120 can be communicated via the network 102. Patients can thus, for example, via use of the dental detection communication device 106, upload the information to the remote treatment system 124, treatment server 138, and/or patient database 140, the requested images, including, for example, photographs, videos, and/or X-rays, among the like at block 312. Moreover, block 312 can be generally similar to at least block 206 of FIG. 2, as discussed above.

At block 314, the remote treatment system 124 can diagnose the information provided at block 312. For example, similar to blocks 208 and 210 of FIG. 2, the remote treatment system 124 can analyze the information using the AI engine 136 as described herein to make the treatment recommendations.

Moreover, the remote treatment system 124, aided by AI engine 136, can analyzes each of these various symptoms, as provided at least at block 312, and determine at block 314 tan associated diagnosis and/or associated severity of the problem, if any, for patients of various ages. At block 314, the AI engine 136 can also recommend, or not recommend, treatment, as well as report, for each treatable symptom, the expected results of treatment, length of treatment and retention. The AI engine 136, or other portions of the remote treatment system 124, can provide such information via use of input from charts, tables, or models, the information, including data, captured in, or attained from, an image(s) of the patient, the history of outcomes, and other historic inputs and outputs tracked in association with treatments over time to assess success and failure in accord with machine learning techniques. Such a process can be implemented for each of the various symptoms referenced herein.

In one embodiment of the disclosure, the remote treatment system 124, including, for example, the AI engine 136, can, upon analysis of the information provided at least at block 312, generate at least one recommendation from a plurality of possible treatment outcomes. For instance, according to a non-limiting example, the remote treatment system 124 and/or the AI engine 136 can be configured to generate one or more recommendations from five possible treatment outcomes, each of which is generally indicated in FIG. 3 as "A", "B", "C", "D", "E".

A first outcome, as indicated in FIG. 3 as outcome "A" (Outcome A) can generally relate to a determination by the AI engine 136 that no treatment is necessary at present. Additionally, Outcome A can also include a suggestion for follow up, in which event the patient can also be information about future treatment and consultation.

A second outcome, as indicated in FIG. 3 as outcome "B" (Outcome B) can relate to the AI engine 136 generating a diagnosis for the patient. Additionally, in connection with such a generated diagnosis, the AI engine 136 can also include with Outcome B a treatment plan/schedule. The patient thus could also be provided by the remote system 124 with additional information regarding the same and consultations.

A third outcome, as indicated in FIG. 3 as outcome "C" (Outcome C) can relate to the AI engine 136 generating a diagnosis, and a referral to a specialist for treatment. Moreover, unlike Outcome B, Outcome C can be related to the determination by the AI engine 136 that the nature of the diagnosis is of a higher complexity than the diagnosis associated with Outcome B In such a situation Outcome C can indicate that the nature of the issue or diagnosis is too complex to be handled by the patient alone or remotely. Outcome C can thus also include information obtained from a referral source as to an identity of a recommended medical professional for the patient to contact, among other information.

A fourth outcome, as indicated in FIG. 3 as outcome "D" (Outcome D) can relate to the AI engine 136 generating a diagnosis, a treatment plan/schedule, and a recommendation that the patient also see a specialist about particular features of the treatment or other matters detected during the analysis that may not be treatable as set forth herein. Thus, similar to Outcome C, Outcome D can include additional information relating at least to a referral from a referral source of an identity of a recommended medical professional for the patient to contact, among other information.

A fifth outcome, as indicated in FIG. 3 as outcome "E" (Outcome E) can relate to the AI engine 136 generating a request that the patient provide additional information for consideration and/or consents. For example, the Outcome E can be generated in response to the AI engine 136 similar information be resubmitted, such as, for example, with respect to providing additional clarification, enhanced image quality, and/or improved positioning for the image. Additionally, or alternatively, Outcome E can be generated in response to the AI engine 136 determining additional information is required or the diagnosis, including, but not limited to, images capturing another, or different tooth/teeth, and/or different types of images or information.

According to certain embodiments, the outcome provided at block 314 can be, but is not necessarily, reviewed, and/or approved, by an overseeing medical professional before being communicated to the patient.

An outcome of the system diagnosis from block 314, such as, for example, one or more of Outcome(s) A, B, C, D, and/or E, as discussed above, among other information, can be retrieved by the patient at block 316. For example, according to certain embodiments, the patient can connected to using the dental detection communication device 106, and via the network 102, to the remote treatment system 122, treatment server 138, and/or the patient database 140 to retrieve an outcome from block 316. Thus, according to certain embodiments, such retrieval of the outcome via use of the dental detection communication device 106 can include, for example, connecting to a website, or activating a link provided to the patient that takes the patient to a website, that is associated with the system 124.

If the patient elects to proceed with a treatment, as provided by the remote treatment system 122, then at block 318 treatment can commence. Such a decision to commence treatment can be communicated electronically to the remote treatment system 124, and can include the patient providing at payment or payment information at either block 316 or block 318. Commencement of treatment can also involve completion of administrative processing, including, for example, registration, of the patient with the remote treatment system 122.

At block 320, the remote treatment system 122 can arrange for one or more orthodontic appliances and instructions associated with the outcome generated at block 316 to be sent to the user, and treatment can begin, and the system would track follow-ups and treatment progress. Additionally, or alternatively, the system 124 can provide measurements for the patient to order the orthodontic appliance. The system 124 can also provide instructions and assistance with application of the orthodontic appliance(s), such as, for example, either through video, printed material, or on line professional consultation, if desired.

Further, similar to blocks 214-220 of FIG. 2, at block 322 patient can provide updated information, including, for example, images, that the AI engine 136 can process in connection with evaluating the progress, if any, of the current course of treatment, and whether to recommend any changes to the treatment. For example, periodically, such as every month, 2 months, or 3 months, among other time intervals, the patient can provide, such as upload, updated or more recent captured patient information, such as images, from the various image-producing procedures described herein, as well as other information through the system portal. The system 124, such as, for example, the AI engine 136 can repeat the diagnostic procedure and report back to the patient on the success, or lack thereof, of the current treatment. If there is a lack of success, the AI engine 136 can operate to update and/or revise the AI engine, including, for example, a model or algorithm being used by the AI engine 136.

Such periodic updating of patient captured information can continue to occur, including for example, in connection with evaluating when treatment is finished, as indicate by block 324. Moreover, similar to blocks 220 and 222 discussed above, at block 324 the AI engine 136 can determine when treatment is to conclude. The conclusion of the treatment can, for example include the system 124 informing the patient the retention of the case, such as, for example, storage of information at the patient database 140, as well as when such retention will expire. Additionally, the system 124 can also request additional images of the patient, such as, for example, x-ray or sonar film, when the patient reaches a certain age. For example, in certain instances, the system 124 can request that the patient provide information when the patient is at about 18 years of age regarding the status of the third molars.

Similar to blocks 220 and 222 discussed above, at block 324 the AI engine 136 can determine when treatment is to conclude.

Additionally, or alternatively, the methods 200, 300 disclosed herein can also include generation, such as, for example, by the AI engine 136, of a rating that can be used in connection with determining of whether a treatment for the patient is recommended, and if so what possible treatment outcome is recommended, for a patient. For example, the remote treatment system 122 can use a points based system, for example, on information provided by the patient at block 204 of FIG. 2 or block 310 of FIG. 3 with respect to patient responses or information to one or more of the above-discussed questionnaires. As previously discussed, such questionnaires can be tailored to the particular patient, including, for example, based on the age of the patient. Therefore, in the below examples, the patient provided information or responses can be based on requested symptom information that is tailored for use with an early developing dentition analysis. According to certain embodiments, implementation of such an approach, or the manner in which the approach is implemented, may be at least partially dependent on an age of the patient. For example, according to certain embodiments, analysis employed for such a rating system for adults may be different than the analysis employed for minors. Moreover, such variances in the analysis can be directed to improving the accuracy of the outcomes for different age groups.

For example, in particular regard to early developing dentition, the system can use symptoms that can have a serious impact on craniofacial development in the earlier age groups, such as patients of age 12 and younger. These symptoms and categorized and discussed below as Group A, Group B, and Group C.

With respect to Group A, a plurality of common symptoms can, when present, be assigned a common value/weight, such as, for example, a value of 5 points each. However, at least one special symptom can be assigned a special value/weight, such as, for example, a value of 25. Additionally, or alternatively, the special value/weight may only apply for a particular common symptom when the patient is not experiencing any other common symptoms. Thus, in some applications, when the patient has one common symptom, that common symptom and the special symptom may each receive the value or weight assigned for special symptoms. Additionally, or alternatively, the value or weight of the special symptom can be changed, such as, for example, reduced, if other special symptoms are identified.

For example, with respect to patients in the age range of 5-12 years old, the symptoms of Group A that can be assigned a common value/weight can include, for example, any combination, if not all, of the following five symptoms: (1) an overbite exceeds a predetermined threshold (e.g. a value greater than 1 mm for patients aged 5-7 years, and a 3 mm overbite for patients aged 8-12 years); (2) an overjet that exceeds a predetermined threshold (e.g. greater than 3 mm); (3) period(s) (e.g. day or night) of mouth breathing (any severity); (4) snoring (any severity); and, (5) period(s) (e.g. day or night) of thumb sucking (any severity). Additionally, Group A can include at least one special symptom, which can be the sixth symptom of Group A, that is assigned a special value/weight, such as, for example, whether the patient does or does not have a cleft lip and palate.

Group B can be particularly applied for assessment of patients of belonging to a younger age group. While Group B contains more symptoms than Group A, Group B identifies less occurring symptoms. Further, one or more of the symptoms listed below for Group B can also be included in the assessments of Group A and C, including being considered as part of the evaluation of common symptoms. Further, each of the below common symptoms can be assigned a weight or value, such as, for example, 3 points. Thus, continuing with the prior age group of 5-12 years, the common symptoms for group B can include a plurality, if not all, of the following common symptoms: cross bite, anterior; cross bite, posterior; Class III, pseudo; Class III, skeletal ($\leq$3 mm); open bite ($\geq$1 mm); crowding (from lower arch length analysis>1 mm); crowding (from upper arch length analysis>1 mm); rotations (broken contacts, lower$\geq$2); rotations (broken contacts, upper$\geq$2); TMJ problems (including minimal opening of 2 fingers of patient); narrow arch, upper (>2 mm); narrow arch, lower (>2 mm);

bruxism, space lower dentition that will not close with eruption of permanent teeth (≥3 mm); space upper dentition that will not close with eruption of permanent teeth (≥3 mm); Midline discrepancy; abnormal swallowing; abnormal tongue thrust; abnormal resting tongue posture; difficult nasal breathing; impossible nasal breathing; abnormal tonsil swelling (Grades 3 and 4); gummy smile (>2 mm in deciduous dentition; >3 mm 8-12 years); periodontal issues; gingival retraction of any lower incisor; and scissors bite; and, tongue tie (must touch palate with tongue when mouth is wide open).

There is a third group of symptoms, namely Group C, are usually obtained by panoramic or cephalometric (or CBCT scans) x-ray films. Continuing with the prior example regarding patients of 5-12 years old, each symptom, also referred to herein as a common symptom, can be given a value or weight, such as, for example, a weight of 2 points each. Group C common symptoms can include, for example: abnormal tooth sizes; abnormal tooth discrepancy (>-1 standard deviation); root resorption of any teeth; abnormal adenoid swelling; abnormal cephalometric measures (SNA, SNB, ANB, Wits Analysis); abnormal facial length (using profile analysis); abnormal facial A-P dimension (using profile analysis); congenitally missing permanent teeth or extracted permanent teeth (not including 3rd molars); supernumerary teeth; impactions of any teeth; excessive >7 mm freeway space; thickness of mandibular body (excessively thin or thick); severe rotations of canines, premolars, molars (>45°); and, cysts, abscesses.

Group A characteristics can be either very severe symptoms or symptoms that have a significant impact on craniofacial development or can result in serious sleep issues that can affect growth and development. Instances in which all six of Group A symptoms are present (e.g. the five above-mentioned common symptoms and the one special symptom), each of the symptoms can rates as 5-point weight/rating. As indicated above, in the case of overbite and overjet, the associated symptoms only qualify as a symptom generating a point value when the predetermined value is exceeded, which in this example, is 3 millimeters (mm) for overbite ages 8-12 years or a 1 mm overbite for ages 5-7 years old, and a overjet that exceeds 3 mm.

Additional criteria or contingencies can also be utilized in the scoring use for the rating for Group A. For example, if only a deciduous or partially deciduous overbite for patients up to 10 years of age is present, then the symptom threshold could have an additional 2 nanometers (nm) added to the predetermined threshold. Further, if the overbite or overjet is equal to or exceeds 5 mm and no other common or special symptoms are present, then overbite or overjet symptom could automatically be assigned a rating of 25 points. The other important symptoms of Group A also require additional rating of 25 points if any one of them is the only common symptom present. Special symptoms, such as cleft lip and palate involving the dentition can always receive the special value or weight, which in this example, is a 25 point rating.

With respect to Group B and Group C, in the illustrated example, all the symptoms of Group B are, when present, assigned the same value or weight, which in this example is 3 points, and Group C symptoms, when present, register a 2 point rating. Further, symptoms for patients aged 5-7 are often generally quite similar to patients having ages of 8-12 years, with the exception of the overbite. Further, as seen above, gummy smile, which is easily corrected, in the 5-7 year old group if it is 2 mm, while in the 8-12 year old group there is only a 1 mm improvement in the gummy smile by 12 years of age. Thus there is no prevention of this symptom between 8 and 12 years of age and, as a result, the amount of severity required is indicated above as greater than 3 mm.

For each patient, the total points from Group A, Group B, and Group C, collectively, can be summed to provide an overall symptom score or rating for a severity index. The system can then evaluate the overall symptom score, or cumulative symptom score, with predetermined ranges of symptom scores to determine a corresponding severity index. Thus, the analysis conducted by the AI engine 136 can consider both the number and severity of symptoms. Further, by combining the number of symptoms with the weighted values, as discussed above with respect to Groups A, B, and C, a more inclusive severity index is generated. Such a severity index can also vary in its impact as a problem or issue with the patient increases, as reflect in an overall influence the problem may have on the patient's health.

Further, according to certain embodiments, the severity indexes can be similar to the five outcomes (Outcomes A-E) that are discussed above with respect to block 314 of FIG. 3. For example, the overall symptom score from Groups A, B, and C, collectively, can be within a point range encompassed by a first severity index, which can correspond to the highest range of overall symptom scores. In such a situation, having an overall symptom score be within the range of the first severity index can provide an indication, such as, for example, to the AI engine 136, that treatment is mandatory and/or that the patient's condition is severe. The next, or second severity index, can correspond to a range of overall symptom scores that are below the first severity index, and can provide an indication to the AI engine 136 that treatment is strongly recommended, and that the patient's condition may be pronounced. The next, or third severity index, which may correspond to a range of overall symptom scores that are below the first and second severity indexes, can indicate to the AI engine 136 that the patient's condition is moderate, and that treatment is recommended. A fourth severity index can also be provide, which can correspond to a range of overall symptom scores that are below the first, second, and third severity indexes, can indicate to the AI engine 136 that the patient's condition is mild, and treatment is optional. Finally, the last, or fifth severity index, can correspond to an indication to the AI engine 136 that treatment is unnecessary, and the condition of the patient, if any, is minor.

Thus, for example, in one example, each of the above-discussed five severity indexes can correspond to a different level, group, or grade of sleep disorder. Further, information regarding attributes of each grade of sleep disorder can be based on historical data that can be built in, or attainable by, the AI engine 136, which can be dynamically updated. Further, each grade of sleep disorder can include information regarding recommended treatments, actual treatments, and treatment results or success, and/or treatment efficiency, which again, can be based on historical information and/or models, including algorithms, developed from such historical information. Such information can be used by the AI engine 136, and as well as presented to a patent in a unique and easily understood and convincing manner that can result in a more intelligent and informative conclusion regarding the treatment recommendations that the system 124 may present to the patient. While the foregoing is discussed in terms of sleep disorders, such a symptom and symptom severity approach can also be utilized by the AI engine 136 in connection with other patient issues and disorders.

An object of the present disclosure is to provide a patient with a complete diagnosis of dentition issues from images created using various image producing procedures taken by the patient.

An object of the present disclosure is to have a computer controlled system, utilizing an artificial intelligence engine, to generate from images of dentition, and other information from a patient, a complete treatment recommendation, treatment procedures and all follow up information without the patient ever having to be treated by a healthcare professional in person.

An object of the present disclosure is to provide a computer system for diagnosis and treatment of an orthodontic condition based on obtaining remote patient records that is more consistent, quicker, complete, and less expensive than can be provided by a healthcare professional.

An object of the present disclosure is to provide a computer system for diagnosis and treatment of an orthodontic condition based on obtaining remote patient records that is objective, free from bias or philosophical treatment preconceptions, and that is not prejudiced by a lack of knowledge, experience, or clinical ability.

An object of the present disclosure is to provide a computer system for diagnosis and treatment of an orthodontic condition based on obtaining remote patient records that analyzes a broader set of symptoms than a dental professional would typically use for a diagnosis, including for example conditions of sleep, speech, tongue use, or other oral habits that are generally not highly regarded by a dental professional.

An object of the present disclosure is to provide a computer system for diagnosis and treatment of an orthodontic condition based on obtaining remote patient records that prescribes specific orthodontic appliance sizes for correction of the condition.

An object of the present disclosure is to provide a computer system for diagnosis and treatment of an orthodontic condition based on obtaining remote patient records that can consider regularly updated records of progress of treatment, and information about the patient's compliance therewith, all done remotely and preferably from the patient's home.

An object of the present disclosure is to provide a computer system for diagnosis and treatment of an orthodontic condition that avoids fixed appliances by orthodontist and is preventive and interceptive in function.

An object of the present disclosure is to provide a computer system for diagnosis and treatment of an orthodontic condition that reduces the likelihood of professionals purposeful falsifying the diagnosis and complicating the treatment to increase a fee.

An object of the present disclosure is to provide a computer system for diagnosis and treatment of an orthodontic condition that provides a non-biased diagnosis in an accurate manner to governmental and insurance agencies that approve treatments and cover the cost of such treatments.

An object of the present disclosure is to provide a computer system for diagnosis and treatment of an orthodontic condition that gives the patient a more comprehensive analysis of the true severity of the issues, and gives the patient an objective idea of the magnitude of the condition in relation to the overall population based on objective data and information.

An object of the present disclosure is to provide a computer system for diagnosis and treatment of an orthodontic condition that gives the patient an idea of how successful the treatment will be based on objective data and analysis.

An object of the present disclosure is to provide a computer system for diagnosis and treatment of an orthodontic condition that gives the patient an idea as to the mean percentage of correction expected.

An object of the present disclosure is to provide a computer system for diagnosis and treatment of an orthodontic condition that gives the patient an idea as to the probability of obtaining 100% treatment success based on objective data and analysis.

An object of the present disclosure is to provide a computer system for diagnosis and treatment of an orthodontic condition that gives the patient an idea of how severe the problem is based on objective data and analysis.

An object of the present disclosure is to provide a computer system for diagnosis and treatment of an orthodontic condition that give the patient an idea of the symptoms present and their severities at various ages.

An object of the present disclosure is to provide a computer system for diagnosis and treatment of an orthodontic condition that gives the patient a prediction at a predetermined confidence level (e.g. 95%) of the likely final result of treatment.

An object of the present disclosure is to provide a computer system for diagnosis and treatment of an orthodontic condition that gives the patient an idea of how serious any speech issues are based on objective data and analysis.

An object of the present disclosure is to provide a computer system for diagnosis and treatment of an orthodontic condition that gives the patient an idea of the different symptoms that are important to health of the patient based on objective data and analysis.

An object of the present disclosure is to provide a computer system for diagnosis and treatment of an orthodontic condition that gives the patient an idea if treatment is worthwhile or not based on objective data and analysis.

An object of the present disclosure is to provide a computer system for diagnosis and treatment of an orthodontic condition that gives the patient more education about the conditions based on objective data and analysis.

An object of the present disclosure is to provide a computer system for diagnosis and treatment of an orthodontic condition that gives the patient a more comprehensive analysis of the condition based on the analysis of more clinical input variables than prior art analysis.

An object of the present disclosure is to provide a computer system for diagnosis and treatment of an orthodontic condition appropriate for the 5-7 year old group that is more accurate than an analysis based on adult dentition applied to the 5-7 year age group.

An object of the present disclosure is to provide a computer system for diagnosis and treatment of an orthodontic condition based on a treatment analysis appropriate for the 8-12 year old group that is more accurate than an analysis based on adult dentition applied to the 8-12 age group.

An object of the present disclosure is to provide a computer system for diagnosis and treatment of an orthodontic condition based on a far more complete and inclusive set of symptoms, and uses a treatment analysis that is more complete than the prior art.

Although the present disclosure has been described with reference to example implementations, workers skilled in the art will recognize that changes may be made in form and detail without departing from the spirit and scope of the claimed subject matter. For example, although different example implementations may have been described as including features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

The invention claimed is:

1. A system for remotely diagnosing and treating a patient by a neural network of an artificial intelligence engine, the system comprising:
   one or more databases that retain historical data for a plurality of patients corresponding to a plurality of historical symptoms, a plurality of historical orthodontic treatment options, and a historical treatment efficiency for each of the plurality of historical orthodontic treatment options, each of the plurality of historical orthodontic treatment options corresponding to at least a combination of a number of historical symptoms of the plurality of historical symptoms and a severity of each of the number of historical symptoms;
   at least one processor;
   a memory device coupled to the at least one processor, the memory device including instructions that when executed by the at least one processor cause the at least one processor to:
   determine a machine learning algorithm for patient diagnosis and treatment recommendations using historical data from the one or more databases for a plurality of patients corresponding to the plurality of historical symptoms, the plurality of historical orthodontic treatment options, and the historical treatment efficiency for each of the plurality of historical orthodontic treatment options, each of the plurality of historical orthodontic treatment options corresponding to at least a combination of a number of historical symptoms of the plurality of historical symptoms and a severity of each of the number of historical symptoms;
   receive a patient captured information, the patient captured information being captured by the patient and comprising at least one image;
   determine at least one measurement using the patient captured information;
   identify at least a patient condition from the patient captured information;
   analyze, for a continuous training of the machine learning algorithm, the historical data to identify one or more patterns that correlate the historical treatment efficiency for the plurality of historical orthodontic treatment options to the historical symptoms;
   identify, using the at least one measurement and the patient condition, and by use of the machine learning algorithm, a recommended treatment option;
   identify, in response to the recommended treatment option, an orthodontic apparatus;
   generate a digital overlay comprising a digital placement of an orthodontic appliance image, corresponding to the orthodontic apparatus, on at least a portion of the at least one image;
   determine, using the digital overlay, a size of the orthodontic apparatus relative to the portion of the at least one image;
   select, for implementation, based at least in part on a result of the determination of the size of the orthodontic appliance image relative to the portion of the at least one image, the orthodontic apparatus for treatment of the patient;
   generate an expected likelihood of success for the treatment of the patient based on at least the orthodontic apparatus selected for implementation, the patient condition, and the historical data from the one or more databases;
   generate a signal to communicate the orthodontic apparatus selected for implementation and the expected likelihood of success to the dental detection communication device.

2. The system of claim 1, wherein the memory device further includes instructions that when executed by the at least one processor cause the at least one processor to identify the orthodontic apparatus corresponding to the recommended treatment option, and communicate the identification of the recommended orthodontic apparatus to the dental detection communication device.

3. The system of claim 2, wherein the size of the orthodontic apparatus is relative to a size of one or more teeth of the patient depicted in the portion of the at least one image.

4. The system of claim 3, wherein the orthodontic apparatus selected for implementation is a first orthodontic apparatus, and wherein the memory device further includes instructions that when executed by the at least one processor cause the at least one processor to identify a second orthodontic apparatus that is to implemented with the first orthodontic apparatus.

5. The system of claim 1, wherein the memory device further includes instructions that when executed by the at least one processor cause the at least one processor to receive an updated patient captured information, the updated patient captured information comprising at least one updated image captured by the patient after an implementation of the recommended treatment option.

6. The system of claim 5, wherein the memory device further includes instructions that when executed by the at least one processor cause the at least one processor to:
   determine, using the at least one updated image and the machine learnable algorithm, a treatment status that indicates an extent, if any, of a change to the patient attributed at least in part to the implementation of the recommended treatment option;
   evaluate, using the machine learnable algorithm, the treatment status with respect to at least the historical treatment efficiency corresponding to the recommended treatment option; and
   output an updated recommendation comprising a selection of another orthodontic treatment option from the plurality of historical orthodontic treatment options.

7. The system of claim 6, wherein the other treatment option comprises an implementation of another orthodontic apparatus.

8. The system of claim 6, wherein the memory device further includes instructions that when executed by the at least one processor cause the at least one processor to analyze, based on a result of the evaluation of the treatment status with the historical treatment efficiency, and for the continuous training of the machine learnable algorithm, the treatment status to identify at least an adjustment for the plurality of historical orthodontic treatment options.

9. The system of claim 1, wherein the memory device further includes instructions that when executed by the at least one processor cause the at least one processor to generate a link to a website at which the patient can retrieve the communication of the recommended orthodontic treatment option patient.

10. The system of claim 1, wherein the memory device further includes instructions that when executed by the at least one processor cause the at least one processor to:
  generate a first link at which the patient uploads at least the patient captured information;
  identify one or more forms that are to be communicated to the patient to obtain the patient input response; and
  generate a second link at which the patient can retrieve the recommended treatment option.

11. The system of claim 10, wherein the memory device further includes instructions that when executed by the at least one processor cause the at least one processor to:
  identify one or more patient symptoms identified in the patient input response;
  identify a value for each of the one or more patient symptoms;
  generate an overall symptom score, the overall symptom score including at least a sum of the values for each of the one or more patient symptoms;
  identify a severity index using the overall symptom score; and
  identify the recommended orthodontic treatment option based at least in part on the severity index.

12. A computer implemented method for remotely diagnosing and treating a patient by a neural network of an artificial intelligence engine, the method comprising:
  determining, by the neural network, a machine learning algorithm for patient diagnosis and treatment recommendations using historical data for a plurality of patients corresponding to a plurality of historical symptoms, a plurality of historical orthodontic treatment options, and a historical treatment efficiency for each of the plurality of historical orthodontic treatment options, each of the plurality of historical orthodontic treatment options corresponding to at least a combination of a number of historical symptoms of the plurality of historical symptoms and a severity of each of the number of historical symptoms;
  receiving, by the neural network, a patient captured information, the patient captured information comprising at least one image and being obtained by the patient;
  determining, from the patient captured information, at least one measurement;
  receiving, by the neural network, a patient input response indicating at least a patient condition;
  analyzing, for a continuous training of the machine learning algorithm, the historical data to identify one or more patterns that correlate the historical treatment efficiency for the plurality of historical orthodontic treatment options to the historical symptoms;
  identifying, using the at least one measurement and the patient input response, and by using the machine learning algorithm, a recommended treatment option;
  identifying, in response to the recommended treatment option, an orthopedic apparatus;
  generating a digital overlay comprising a digital placement of an orthodontic appliance image, corresponding to the orthodontic apparatus selected in response to the recommended treatment option, on at least a portion of the at least one image;
  determining, using the digital overlay, a size of the orthodontic appliance image relative to the portion of the at least one image;
  selecting for implementation, based at least in part on a result of the determined size of the orthodontic appliance image relative to the portion of the at least one image, the orthodontic apparatus for treatment of the patient;
  generating an expected likelihood of success for the treatment of the patient based on at least the orthodontic apparatus selected for implementation, the patient condition, and the historical data from the one or more databases; and
  generating a signal to communicate the orthodontic apparatus selected for implementation and the expected likelihood of success to the dental detection communication device.

13. The computer implemented method of claim 12, further comprising:
  identifying, by the machine learning algorithm, the orthodontic apparatus corresponding to the recommended treatment option; and
  communicating the identification of the recommended orthodontic apparatus for the patient.

14. The computer implemented method of claim 13, wherein determining the size of the orthodontic appliance image relative to the portion of the at least one image comprises comparing the size of the orthodontic apparatus to one or more teeth of the patient depicted in the portion of the at least one image.

15. The computer implemented method of claim 12, further comprising:
  receiving, by the neural network, an updated patient captured information, the updated patient captured information being obtained by the patient and comprising at least one updated image captured after an implementation of the recommended treatment option.

16. The computer implemented method of claim 15, further comprising:
  determining, by the machine learning algorithm using the at least one updated image, a treatment status that indicates an extent, if any, of a change to the patient attributable to the implementation of the recommended treatment option;
  evaluating, by the machine learning algorithm, the treatment status with the historical treatment efficiency corresponding to the recommended treatment option; and
  outputting an updated recommendation comprising a selection of another orthodontic treatment option from the plurality of historical orthodontic treatment options.

17. The computer implemented method of claim 16, further comprising identifying, based on a result of the evaluation of the treatment status with the historical treatment efficiency, another recommended orthodontic treatment option from the plurality of historical orthodontic treatment options.

18. The computer implemented method of claim 16, further comprising, analyzing for continuous training of the by the machine learning algorithm, and based on a result of the evaluation of the treatment status with the historical treatment efficiency, the treatment status to identify at least an adjustment for the recommended treatment option.

19. The computer implemented method of claim 12, further comprising:
   generating a first link at which the patient uploads at least the patient captured information;
   identifying one or more forms that are to be communicated to the patient to obtain the patient input response; and
   generate a second link at which the patient can retrieve the recommended treatment option.

20. The computer implemented method of claim 19, further comprising:
   identifying one or more patient symptoms identified in the patient input response;
   identifying a value for each of the one or more patient symptoms;
   generating an overall symptom score, the overall symptom score including at least a sum of the values of the one or more patient symptoms;
   identifying a severity index for the patient using the overall symptom score; and
   identifying the recommended orthodontic treatment option based at least in part on the severity index.

* * * * *